United States Patent [19]
Eggler et al.

[11] Patent Number: 5,384,318
[45] Date of Patent: Jan. 24, 1995

[54] SUBSTITUTED SULFONAMIDES AND RELATED COMPOUNDS IN THE TREATMENT OF ASTHMA, ARTHRITIS AND RELATED DISEASES

[75] Inventors: James F. Eggler, Stonington; Anthony Marfat, Mystic; Lawrence S. Melvin, Jr., Ledyard; Hiroko Masamune, Noank, all of Conn.

[73] Assignee: Pfizer Inc., New York, N.Y.

[21] Appl. No.: 835,997

[22] PCT Filed: Jun. 22, 1989

[86] PCT No.: PCT/US89/02748

§ 371 Date: Feb. 21, 1992

§ 102(e) Date: Feb. 21, 1992

[51] Int. Cl.$^6$ ............... C07D 215/14; C07D 401/06; A61K 31/47

[52] U.S. Cl. ............ 514/212; 514/259; 514/312; 514/314; 514/367; 540/480; 540/481; 540/593; 544/283; 544/284; 546/153; 546/155; 546/165; 546/172; 546/175; 548/159

[58] Field of Search ........... 548/159; 540/480, 481, 540/593; 544/283, 284; 546/153, 155, 165, 172, 175; 514/212, 259, 312, 314, 367

[56] References Cited

PUBLICATIONS

Ann F. Welton, George W. Holland, Douglas W. Morgan, and Margaret O'Donnell, Pulmonary and Antiallergy Agents, 24 Annual Reports in Medicinal Chemistry 61–70 (1989).

Hiroko Masamune and Lawrence S. Melvin, Jr., Novel Applications of Leukotriene Intervention, 24 Annual Reports In Medicinal Chemistry 71–79 (1989).

Stevan W. Djuric, Timothy S. Gaginella, Donald J. Fretland and Peter H. Jones, Recent Advances i the Treatment of Inflammatory Bowel Disease, 24 Annual Reports In Medicinal Chemistry 167–175 (1989).

Ellen L. Smith and John J. Tegeler, Advances in Dermatology, 24 Annual Reports in Medicinal Chemistry 177–186 (1989).

*Primary Examiner*—Robert Gerstl
*Attorney, Agent, or Firm*—Peter C. Richardson; Paul H. Ginsburg; Garth C. Butterfield

[57] ABSTRACT

Compounds of the formula

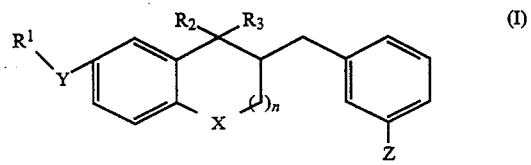

and pharmaceutical compositions comprising them, wherein $R^1$, $R^2$, $R^3$, W, X and Z are as defined below. The compounds are inhibitors of 5-lipoxygenase enzyme and antagonists of leukotriene B4, leukotriene C4, leukotriene D4 and leukotriene E4.

12 Claims, No Drawings

SUBSTITUTED SULFONAMIDES AND RELATED COMPOUNDS IN THE TREATMENT OF ASTHMA, ARTHRITIS AND RELATED DISEASES

BACKGROUND OF THE INVENTION

The present invention is directed to substituted sulfonamides and related compounds of the formula I, depicted below, which by inhibiting 5-lipoxygenase enzyme and/or blocking leukotriene receptors, are useful in the prevention or treatment of asthma, arthritis, psoriasis, ulcers, myocardial infarction, stroke, irritable bowel disease and related disease states in mammals. The present invention is also directed to pharmaceutical compositions of, and a method of treatment using said compounds of formula (I).

It is known that leukotrienes are compounds produced in mammals by the metabolism of arachidonic acid. Arachidonic acid is metabolized in mammals by means of two distinct pathways, one leading to prostaglandins and thromboxanes, and the other to several oxidative products known as leukotrienes, which are designated by letter-number combinations such as leukotriene B4 (LTB4), leukotriene C4 (LTC4) and leukotriene D4 (LTD4). The first step in this oxidative pathway is the oxidation of arachidonic acid under the influence of 5-lipoxygenase enzyme, an enzyme which is generally inhibited by the compounds of the present invention, thus blocking the synthesis of all leukotrienes. That in itself provides the mechanism sufficient for the utility of these compounds in the treatment or prevention of asthma (where LTC4 and LTD4 are understood to be mediators), arthritis (where LTB4 is understood to be a mediator), psoriasis (where LTB4 is understood to be a mediator), ulcers (where LTC4 and LTD4 are understood to be mediators), myocardial infarction (where LTB4 is understood to be a mediator), stroke (where LTD4 is understood to be a mediator) and irritable bowel disease (where LTB4 is understood to be a mediator). Supplementing this enzyme inhibitory activity is the general ability of the present compounds to antagonize (i.e., to block receptors of) LTB4, LTC4, LTD4 and LTE4. For a review concerning leukotrienes, see Bailey et al., *Ann. Reports Med. Chem.* 17, pp. 203–217 (1982).

Eggler et al., in PCT Patent Application PCT/US87/02745, describe racemic or optically active substituted tetralins, chromans and related compounds that inhibit 5-lipoxygenase enzyme and antagonize LTB4 and LTD4, and are therefore useful in the prevention and treatment of asthma, arthritis, psoriasis, ulcers, and myocardial infarction.

Kreft et al., in U.S. Pat. No. 4,661,596, describe disubstituted naphthalenes, dihydronaphthalenes and tetralins that inhibit lipoxygenase enzyme and antagonize LTD4, and are therefore useful in the prevention and treatment of asthma.

SUMMARY OF THE INVENTION

The present invention relates to compounds of the formula

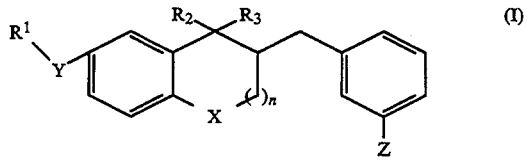

wherein
$R^1$ is quinolyl, substituted quinolyl, benzothiazolyl, substituted benzothiazolyl, benzopyrimidinyl, or substituted benzopyrimidinyl, wherein said substituted quinolyl, substituted benzothiazolyl, and substituted benzopyrimidinyl are substituted with one or more substituents that are independently selected from the group consisting of fluoro, bromo, chloro, phenyl, hydroxy, trifluoromethyl and $(C_1–C_4)$ alkyl;

$R^2$ and $R^3$ are each H or OH;

Y is $CH_2O$, $C_2H_4$ or $C_2H_2$;

X is $CH_2$, O, S, NH or $NR^7$;

$R^7$ is $(C_1–C_4)$ alkyl;

n is an integer from 0–3;

Z is CONHW or $CON(Me)_2$;

W is $SO_2Q$, COQ or Q; and

Q is hydrogen, phenyl, substituted phenyl, $(C_1–C_8)$ alkyl, cycloalkyl, tetrazolyl, or thiazolyl, wherein the foregoing substituted phenyl groups are substituted with one or more substituents independently selected from the group consisting of chloro, fluoro and $(C_1–C_4)$ alkoxy;

and the pharmaceutically acceptable acid addition and cationic salts thereof.

Preferred compounds of the invention are compounds of the formula I wherein $R^1$ is 5-fluoro-2-benzothiazolyl, X is O, $r^2$ is hydrogen, n=1, $R^3$ is hydroxy, and Z is independently selected from the group consisting of carboxamide, N-methanesulfonyl carboxamide, N-acetyl carboxamide, and N-tetrazoyl caboxamide.

A more preferred compound of the invention is the compound having formula I wherein $R^1$, $R^2$, $R^3$, X and n are as defined in the preceding paragraph, and Z is N-phenylsulfonyl carboxamide.

Specific compounds of the invention are
cis-3-[7-[(5-fluoro-2-benzothiazolyl)methoxy]-4,5-dihydro-5-hydroxy-2H-1-benzohomopyran-4-ylmethyl]-N-(phenylsulfonyl)benzamide, cis-3-[6-[(2-quinolinyl)methoxy]-3,4-dihydro-4-hydroxy-2H-1-benzopyran-3-ylmethyl]-N-(phenylsulfonyl)-benzamide, cis-3-[6-[(6-fluoro-2-quinolinyl)methoxy]-3,4-dihydro-4-hydroxy-2H-1-benzopyran-3-ylmethyl]-N-(methanesulfonyl)benzamide, cis-3-[6-[(6-fluoro-2-quinolinyl)methoxy]-3,4-dihydro-4-hydroxy-2H-1-benzopyran-3-ylmethyl]-N-(2-methylphenylsulfonyl)benzamide, cis-3-[7-[(5-fluoro-2-benzothiazolyl)methoxy]-4,5-dihydro-5-hydroxy-2H-1-benzohomopyran-4-ylmethyl]-N-(methanesulfonyl)benzamide, cis-3-[6-[(5-fluoro-2-benzothiazolyl)methoxy]-4-hydroxy-1,2,3,4-tetrahydronaphthalen-3-ylmethyl]-N-(methanesulfonyl)benzamide, cis-3-[6-[(2-quinolinyl)methoxy]-4-hydroxy-1,2,3,4-tetrahydronaphthalen-3-ylmethyl]-N-(phenylsulfonyl)benzamide, cis-3-[6-[(2-quinolinyl)methoxy]-3,4-dihydro-4-hydroxy-2H-1-benzopyran-3-ylmethyl]-benzamide, cis-3-[5-[(5-fluoro-2-benzothiazol)methoxy]-3-hydroxyindan-2-ylmethyl]-N-(phenylsulfonyl)benzamide, cis-3-[7-[(2-quinolinyl)methoxy]-4,5-dihydro-5-hydroxy-2H-1-benzohomopyran-4-ylmethyl]-N-(methanesulfonyl)benzamide, cis-3-[6-[(2-quinolinyl)methoxy]-4-hydroxy-1,2,3,4-tetrahydroquinolin-3-ylmethyl]-N-(phenylsulfonyl)benzamide, and cis-3-[6-[(6-fluoro-2-quinolinyl)vinyl]-3,4-dihydro-4-hydroxy-2H-1-benzopyran-3-ylmethyl]-N-(2-methylphenylsulfonyl)benzamide.

The preferred stereochemical configurations for the compounds of this invention in which $R^2$ is hydrogen and $R^3$ is hydroxy are those in which the hydroxy group is cis to the substituted benzyl side chain on the adjacent carbon, i.e. the hydroxy group and the substituted benzyl side chain are either both above or both below the plane of the heterocyclic ring to which they are attached.

The compounds of formula I have optical centers and therefore occur in different stereoisomeric configurations. The invention includes all stereoisomers of such compounds of formula I, including racemic mixtures thereof.

The invention also relates to pharmaceutical compositions for administration to a mammal which comprise a compound of the formula I or a pharmaceutically acceptable acid addition or cationic salt thereof and a pharmaceutically acceptable carrier. Said pharmaceutically acceptable acid addition salts include, but are not limited to those with HCl, HBr, $HNO_3$, $H_2SO_4$, $H_3PO_4$, $CH_3SO_3H$, $p\text{-}CH_3C_6H_4SO_3H$, $CH_3CO_2H$, gluconic acid, tartaric acid, maleic acid, and succinic acid. In the case of those compounds of the formula I which contain a further basic nitrogen, it will, of course, be possible to form diacid addition as well as monoacid addition salts. Said pharmaceutically-acceptable cationic salts include, but are not limited to those of sodium, potassium, calcium, magnesium, ammonia, N,N'-dibenzylethylenediamine, N-methyl-glucamine (meglumine), ethanolamine, and diethanolamine.

The invention further relates to a method of treating or preventing asthma, arthritis, psoriasis, gastrointestinal ulcers, myocardial infarction, stroke or irritable bowel disease, comprising administering to a mammal in need of such treatment or prevention a compound of formula I in an amount effective to treat or prevent such disease.

DETAILED DESCRIPTION OF THE INVENTION

The following reaction schemes illustrate the preparation of the compounds of formula I. For purposes of illustrating different methods of preparation, these compounds are subdivided into compounds of formula IA and compounds of formula IB.

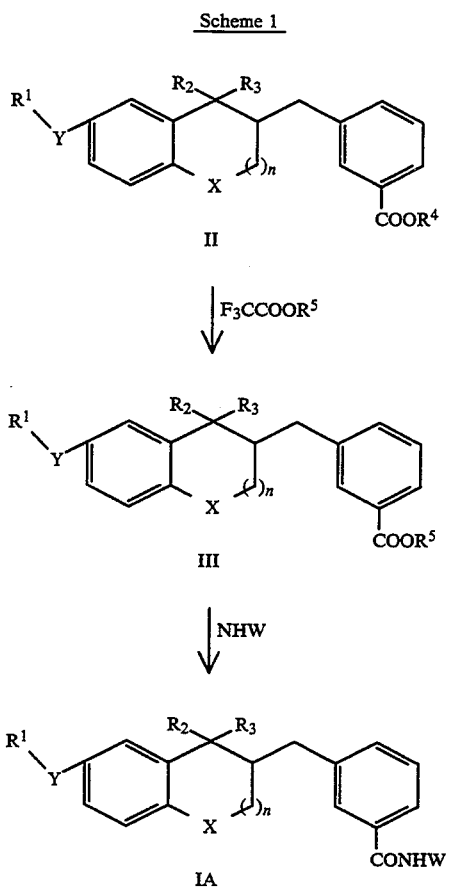

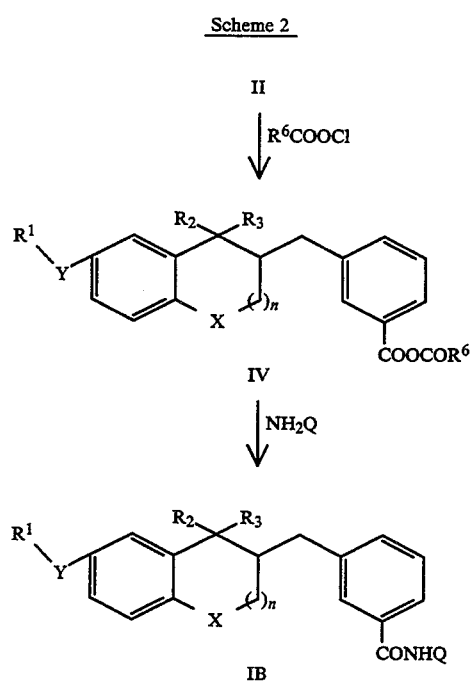

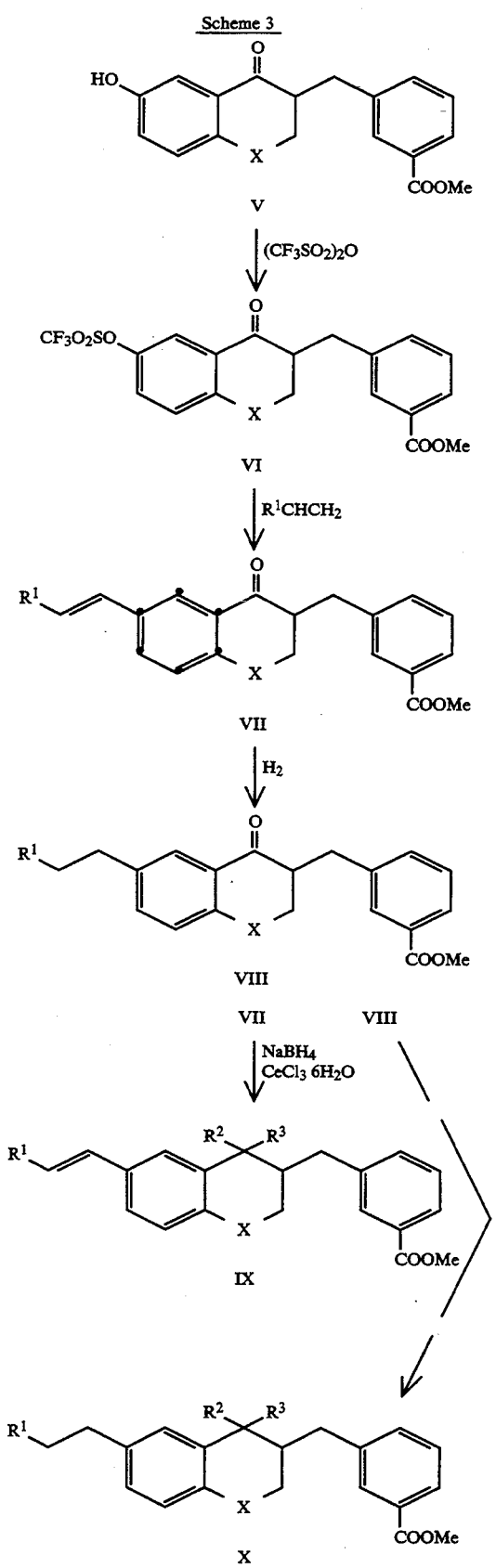

Compounds of the formula IA, wherein $R^1$, $R^2$, $R^3$, X, n and W are as defined above, are typically prepared by reacting an ester of the formula III, wherein $R^1$, $R^2$, $R^3$, X, and n are as defined above and $R^5$ is p-nitrophenyl, with a compound having the formula NHW, wherein W is as defined above, in a reaction inert solvent. Preferred solvents are tetrahydrofuran and p-dioxane. Other suitable solvents are benzene, 1,2 dimethoxyethane ethane and toluene. Temperature is not critical, e.g. about 0°–100° C. is satisfactory, with ambient temperature being preferable as a matter of convenience.

As used herein, "reaction inert solvent" refers to a solvent which does not interact with starting materials, reagents, intermediates or products in a manner that adversely affects the yield of the desired product.

The ester of the formula III is prepared by reacting a compound having formula II wherein $R^1$, $R^2$, $R^3$, X, and n are as defined above and $R^4$ is hydrogen, with a compound of the formula $F_3CCOOR^5$ wherein $R^5$ is p-nitrophenyl, in a reaction inert solvent. The preferred solvent for this reaction is pyridine. Temperature is not critical, e.g. about 0°–100° C. is satisfactory, with ambient temperature being preferable as a matter of convenience.

Compounds of the formula IB wherein $R^1$, $R^2$, $R^3$, X, n and Q are as defined above, can be prepared as described above for the preparation of compounds of formula IA, by using a reactant of the formula NHW, wherein W is Q. Compounds of the formula IB can be prepared, alternatively, as shown in Scheme 2, from an anhydride intermediate having formula IV. This is done as follows A compound of the formula II wherein $R^1$, $R^2$, $R^3$, $R^4$, X and n are as defined above, is reacted with a compound of the formula $R^6COOCl$, wherein $R^6$ is isobutyl, in the presence of a base such as triethylamine and in a reaction inert solvent, after which a compound of the formula NHQ, wherein Q is as defined above, is added to the reaction mixture. The preferred solvent is tetrahydrofuran. Suitable temperatures are those in the range of about 0°–30° C., with 0° C. being preferred.

Compounds of the invention having the formula I, wherein Z is $CON(Me)_2$ may be prepared in a similar manner to the preparation of compounds of the formula IB according to Scheme 2, but using $NH(Me)_2$ as a reactant instead of NHQ.

Compounds of the formula II (the starting material used in Schemes 1 and 2), wherein Y is $CH_2O$, may be prepared as described in PCT Application PCT/US 87/02795. Compounds of the formula II, wherein Y is $C_2H_2$ or $C_2H_4$, may be prepared as shown in part in Scheme 3 and described below.

A compound of the formula V is reacted with trifluoromethanesulfonic anhydride in a reaction inert solvent and in the presence of an acid scavenger, to form a compound of the formula VI. Temperatures from about −78° to 0° C. are suitable, with −78° to −60° C. being preferred. The preferred solvent is dichloromethane. The preferred acid scavenger is triethylamine, though other scavengers such as N,N-dimethylamino pyridine and pyridine may also be used. The compound of the formula VI so prepared is then reacted with a compound of the formula $R^1CHCH_2$, e.g. 2-vinyl-5 fluorobenzothiazole, in the presence of (triphenylphosphine)palladium (II) chloride, triethylamine and tri-o-tolylphosphine in a reaction inert solvent, preferably dimethylformamide, at a temperature from about 50° to 150° C., to produce a compound of the formula VII. Temperatures from 130°–150° C. are preferred. The reaction is preferably carried out in a sealed tube and in a nitrogen atmosphere. The compound of the formula VII so prepared may be converted to the corresponding compound of the formula VIII by reducing it with hydrogen in a reaction inert solvent and in the presence of a palladium/carbon catalyst. The reaction is preferably carried out at a pressure of from about 15 to 40 psi. Methanol is the preferred solvent, though other suitable solvents such as ethyl acetate may also be used.

Compounds of the formulae VII and VIII may be reduced to form, respectively, compounds of the formulae IX and X by reacting them with sodium borohydride and cerium chloride hexahydrate in a reaction inert solvent, preferably methanol, at a temperature from about $-78°$ to $30°$ C. Temperatures from $25°$ to $30°$ C. are preferred. The compounds of the formulae IX and X so formed may be converted to the corresponding carboxylic acids of the formula II by hydrolysis with sodium hydroxide in methanol.

In each of the reactions referred to above, pressure is not critical. Except where otherwise noted, pressures in the range of 1–2 atm are suitable, and ambient pressure is preferred as a matter of convenience.

The novel compounds of formula I are useful as inhibitors of 5-lipoxygenase enzyme and antagonists of leukotriene B4, leukotriene C4, leukotriene D4 and leukotriene E4.

The in vitro activity of the compounds of formula I may be tested as follows. RBL-1 cells, maintained in monolayer form are grown for 1 or 2 days in spinner culture in Minimum Essential Medium (Eagle) with Earl's Salts plus 15% Fetal Bovine Serum supplemented with antibiotic/antimycotic solution (GIBCO). The cells are washed 1 time with RPMI 1640 (GIBCO) and resuspended in RPMI 1640 plus 1 microM glutathione to a cell density of $1 \times 10$ cells/ml. A volume of 0.5 ml of the cell suspension is incubated at $30°$ C. with 0.001 ml of dimethylsulfoxide solution of drug for 10 minutes. The reaction is started by a simultaneous addition of 0.005 ml (14C)-arachidonic acid in ethanol and 0.002 ml A23187 in dimethylsulfoxide to give final concentrations of 5.0 and 7.6 microM, respectively. After a 5 minute incubation at $30°$ C., the reaction is stopped by the addition of 0.27 ml acetonitrile/acetic acid (100/0.3) and the media is clarified by centrifugation. Analysis of the product profile is made by a 0.2 ml injection of the clarified supernatant into HPLC. The separation of radioactive products is effected on a radial PAX CN column (5 mm I.D., Waters) with a solvent systems of acetonitrile/$H_2O$/ acetic acid (0.1%) with a linear acetonitrile gradient from 35% to 70% over 15 minutes at 1 ml/minute. Quantitation is accomplished with a Berthold Radioactivity Monitor equipped with a built-in integrator and a 0.2 ml flow cell mixing 2.4 ml/minute Omnifluor (NEN) with column effluent. Integration units for each product are calculated as a percentage of total integration units, and then compared to the average control levels. The results are expressed as "Percent of Control" and are plotted vs the log of drug concentration. The $IC_5$ values are estimated by graphical inspection.

The ability of the compounds of formula I to compete with radiolabelled LTB4, LTC4, LTD4 and LTE4 for specific receptor cites on guinea pig lung membranes may be tested as described by Cheng et al, Biochemical and Biophysical Research Communication, 118, 1, 20–26 (1984).

To evaluate the compounds of the formula (I) in vivo, they are tested by the so-called PAF lethality assay procedure:

Materials

Mice: DCl males, all approximately the same weight (approximately 26 grams), 12 per group.

Vehicle for oral drug dosing: EES (5% ethanol, 5% emulphor, 90% saline). Stored at room temperature.

Drugs: For routine screening at 50 mg/kg, 20 mg drug is dissolved in 4 ml EES, using sonication in a sonicator bath or grinding in a Ten Broeck grinder to dissolve drug if necessary. If solubility is still a problem, the drug is used as a suspension.

Vehicle for i.v. Injection: Saline with 2.5 mg/ml Bovine Serum Albumin (BSA, Sigma #A4378) and 0.05 mg/ml Propranolol (Sigma #P0884). Prepared fresh daily and kept at room temperature.

Platelet Activating Factor (PAF): A 10 microM stock solution is prepared by dissolving 1 mg PAF (Calbiochem #429460) in 0.18 ml ethanol. This is stored at $-20°$ C. and is diluted in vehicle (see above) the day of use. The concentration of PAF used is calibrated so that when injected at 0.1 ml/10 grams body weight, it will kill approximately 80% of untreated controls. This is usually about 0.028 g/kg (a 1 to 2034 dilution from stock). The solution is prepared in glass containers and is used with glass syringes to minimize surface adhesion by the PAF. It is kept at room temperature.

Positive Control: Phenidone is used at 25 mg/kg (its approximate ED 50).

Method 45 minutes before PAF injection, mice are treated orally with drug using 0.1 ml/10 grams body weight. 35 to 40 minutes they are placed under a heat lamp to dilate the caudal vein for PAF injection. PAF is injected i.v. at 0.1 ml/10 grams body weight, and death follows usually within 30 minutes, rarely after 60 minutes. Results are expressed as percent mortality as compared to controls. Because the assay appears to be sensitive to endogenous catecholamines (i.e., beta agonists protect the mice), Propranolol is used to overcome this potential problem. It also helps if the mice are acclimated to the room before testing, and if room noise and temperature are kept moderate and constant. The heat lamp distance should be calibrated so as to permit vasodilation without visible stress to the mice. Fasting the mice should be avoided.

Variations:
1. The time for oral dosing can be changed.
2. Intravenous drug dosing is possible by coinjecting the drug with PAF in the same volume and vehicle as described above. For coinjection, PAF is prepared at twice the desired concentration in saline with BSA and Propranolol as above, and the drug is prepared at twice the desired concentration in the same vehicle. The two preparations are mixed in equal volumes immediately before injection.

For use in the prevention or treatment of asthma, arthritis, psoriasis, gastrointestinal ulcers, or mycardial infarction in a mammal, including man, a compound of the formula I is given in an amount effective to treat any one of such diseases, and of about 0.5 to about 50 mg/kg/day, in single or divided daily doses. A more preferred dosage range is about 2 to about 20 mg/kg/day, although in particular cases, at the discretion of the attending physician, doses outside the broader range may be required. The preferred route of administration is generally oral, but parenteral administration (e.g., intramuscular, intravenous, intradermal) will be preferred in special cases, e.g., where oral absorption is impaired as by disease, or the patient is unable to swallow. The compounds of formula I can also be administered topically, e.g. to treat psoriasis, or in an aerosol, e.g. to treat asthma.

The compounds of the present invention are generally administered in the form of pharmaceutical compositions comprising at least one of the compounds of the formula I, together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelatin capsules, suspensions, granules, powders and the like; and, for parenteral administration, in the form of injectable solutions or suspensions, and the like; for topical administration, in the form of a gel, lotion or cream; and for administration by inhalation, in the form of an aerosol spray.

The present invention is illustrated by the following examples, but is not limited to the details thereof.

EXAMPLE 1

Cis-3-[[6-[(5-fluoro-2-benzothiazolyl)methoxy]-3,4-dihydro-4-hydroxy-2H-1-benzopyran-3-yl]methyl]-N-(methanesulfonyl)benzamide 314 milligrams sodium hydride was added to a solution containing 1.13 grams methane sulfonamide in 40 ml tetrahydrofuran. The reaction mixture was allowed to stir at room temperature overnight. 1.18 grams cis-4-nitrophenyl-3-[[6-[(5-fluoro-2-benzothiazoly)methoxy]-3,4-dihydro-4-hydroxy-2H1-benzopyran-3-yl]methyl] benzoate was added in one portion and the reaction mixture was allowed to stir an additional 24 hours. The mixture was then quenched with water, acidified to pH 3 and extracted with ethyl acetate. The ethyl acetate extracts were dried over sodium sulfate and evaporated to give 1.2 grams of crude product. The crude product was purified by column chromatography on silica gel eluting with methylene dichloride/ethyl acetate to give 670 mg of product. Recrystallization from tetrahydrofuran/ethyl acetate gave 385 mg of product, m.p. 185°–186° C.

Mass Spectrum: Calc'd for $C_{26}H_{22}N_2O_5SF$, 524.0876. Found, 524.0920.

EXAMPLE 2

Cis-3-[[6-[5-fluoro-2-benzothiazolyl)methoxy]-3,4-dihydro-4-hydroxy-2H-1-benzopyran-3-yl]methyl]-N-(acetyl)benzamide Synthesis was carried out as in example 1, but using 0.85 grams acetamide instead of methane sulfonamide. From 1.18 grams cis-4-nitrophenyl-3-[[6-[(5-fluoro-2-benzothiazolyl)methoxy]-3,4-dihydro-4-hydroxy-2H-1-benzopyran-3-yl]methyl]benzoate, there was obtained 173 milligrams of product, m.p. 191°–190° C.

EXAMPLE 3

Cis-3-[[6-[(5-fluoro-2-benzothiazolyl)methoxy]-3,4-dihydro-4-hydroxy-2H-1-benzopyran-3-yl]methyl]-N-(2-methylbenzoyl)benzamide Synthesis was carried out as in example 1, but using 1.93 grams o-toluamide instead of methane sulfonamide. From 1.17 grams cis-4-nitrophenyl-3[[6-[(5-fluoro-2-benzothiazolyl)methoxy]-3,4-dihydro-4-hydroxy-2H-1-benzopyran-3-yl]methyl]benzoate, there was obtained 550 milligrams of product, m.p. 139°–141° C.

EXAMPLE 4

Cis-3-[[6-[(5-fluoro-2-benzothiazolyl)methoxy]-3,4-dihydro-4-hydroxy-2H-1-benzopyran-3-yl]methyl]-N-(phenylsulfonyl)benzamide Synthesis was carried out as in example 1, but 2.22 grams benzenesulfonamide was used instead of methanesulfonamide. From 1.17 grams cis-4-nitrophenyl-3-[[6-[(5-fluoro-2-benzothiazolyl)methoxy]-3,4-dihydro-4-hydroxy-2H-1-benzopyran-3-yl]methyl]benzoate, there was obtained 436 milligrams of product, m.p. 174°–175° C.

EXAMPLE 5

(+)-Cis-3-[[6-[(5-fluoro-2-benzothiazolyl)methoxy]-3,4-dihydro-4-hydroxy-2H-1-benzopyran-3-yl]methyl]-N-(methanesulfonyl)benzamide Synthesis was carried out as in example 1, but using 1.7 grams optically pure (+)cis-4-nitrophenyl-3-[[6-[(5-fluoro-2-benzothiazolyl)methoxy]-3,4-dihydro-4-hydroxy-2H-1-benzopyran-3-yl]methyl]benzoate, 410 milligrams sodium hydride and 1.65 grams methanesulfonamide. 187 milligrams of product was obtained. $\alpha_D = 33.4°$; $c = 0.005$ in tetrahydrofuran.

EXAMPLE 6

(−)-Cis-3-[[6-[(5-fluoro-2-benzothiazolyl)methoxy]-3,4-dihydro-4-hydroxy-2H-1-benzopyran-3-yl]methyl]-N-(methanesulfonyl)benzamide Synthesis was carried out as in example 1, but using 460 milligrams optically pure (−)cis-4-nitrophenyl-3-[[6-[(5-fluoro-2-benzothiazolyl)methoxy]-3,4-dihydro-4-hydroxy-2H-1-benzopyran-3-yl]methyl]benzoate, 1.18 grams methane sulfonamide and 324 milligrams sodium hydride. 260 milligrams of product was obtained. $\alpha_D = -35.9°$; $c = 0.005$ in tetrahydrofuran.

EXAMPLE 7

Cis-3-[[6-[(5-fluoro-2-benzothiazolyl)methoxy]-3,4-dihydro-4-hydroxy-2H-1-benzopyran-3-yl]methyl]-N-(tetrazolyl)benzamide Synthesis was carried out as in example 1, but using 1.45 grams 5-amino tetrazole monohydrate instead of methanesulfonamide, and using 314 milligrams sodium hydride. From 1.17 grams cis-4-nitrophenyl-3-[[6-[(5-fluoro-2-benzothiazolyl)methoxy]-3,4-dihydro-4-hydroxy-2H-1-benzopyran-3-yl]methyl]benzoate, there was obtained 108 milligrams of product, m.p. 166°–168° C.

EXAMPLE 8

(+)-Cis-3-[[6-[(5-fluoro-2-benzothiazolyl)methoxy]-3,4-dihydro-4-hydroxy-2H-1-benzopyran-3-yl]methyl]-N-(phenylsulfonyl)benzamide Synthesis was carried out as in example 1 but using 2.2 grams benzene sulfonamide instead of methane sulfonamide. From 1.07 grams optically pure (+) cis-4-nitrophenyl-3-[[6-[(5-fluoro-2-benzothiazolyl)methoxy]-3,4-dihydro-4-hydroxy-2H-1-benzopyran-3-yl]methyl]benzoate, there was obtained 243 milligrams of product, m.p. 169°-169.5° C. $a_D = +33.2°$; c=0.005 in tetrahydrofuran.

EXAMPLE 9

(−)-Cis-3-[[6-[(5-fluoro-2-benzothiazolyl)methoxy]-3,4-dihydro-4-hydroxy-2H-1-benzopyran-3-yl]methyl]-N-(phenylsulfonyl)benzamide Synthesis was carried out as in example 1, but using 4.4 grams benzene sulfonamide instead of methane sulfonamide, and using 2.4 grams optically pure (−) cis-4-nitrophenyl-3-[[6-[(5-fluoro-2-benzothiazolyl)methoxy]-3,4-dihydro-4-hydroxy-2H-1-benzopyran-3-yl]methyl]benzoate and 628 milligrams sodium hydride. There was obtained 1.02 grams of product, m.p. 161°-162° C. $a_D = -30°$; c =0.005 in tetrahydrofuran.

EXAMPLE 10

Cis-3-[[6-[(5-fluoro-2-benzothiazolyl)methoxy]-3,4-dihydro-4-hydroxy-2H-1-benzopyran-3-yl]methyl]benzamide 710 milligrams cis-4-nitrophenyl-3-[[6-[(5-fluoro-2-benzothiazolyl)methoxy]-3,4-dihydro-4-hydroxy-2H-1benzopyran-3-yl]methyl]benzoate was dissolved in 10 milliliters of tetrahydrofuran and 30 milliliters of ether and was cooled to −65° C. An excess of anhydrous ammonia was bubbled into the reaction mixture for 1 minute. The reaction mixture was then allowed to stir to room temperature. The volatiles were evaporated and the residue was dissolved in ethyl acetate and washed with a 10 percent sodium hydroxide solution. The ethyl acetate layer was then dried over sodium sulfate and evaporated to give 510 milligrams of crude product. The crude product was recrystallized from acetone to give 225 milligrams of product, m.p. 193°-194° C.

Mass spectrum: Calculated for $C_{25}H_{21}N_2O_4FS$, 464.1206. Found, 464.1197.

EXAMPLE 11

Cis-3-[[6-[(5-fluoro-2-benzothiazolyl)methoxy]-3,4-dihydro-4-hydroxy-2H-1-benzopyran-3-yl]methyl]-N,N-dimethylbenzamide 364 milligrams triethylamine was added to a solution containing 1.5 grams cis-4-nitrophenyl-3-[[6-[(5-fluoro-2-benzothiazolyl)methoxy]-3,4-dihydro-4-hydroxy-2H-1-benzopyran-3-yl]methyl]benzoate in tetrahydrofuran at 0° C. After stirring for 5 minutes at 0° C., a solution of isobutylchloroformate in 5 milliliters of tetrahydrofuran was added dropwise. After stirring at 1° C. for 15 minutes, 364 milligrams anhydrous dimethylamine was bubbled into the reaction mixture for 1-2 minutes. The reaction mixture was allowed to warm to room temperature and the volatiles were evaporated. The residue was purified by chromatography on silica gel eluting with methylene dichloride/ethyl acetate to give 535 mg of product.

Mass spectrum: Calculated for $C_{27}H_{25}N_2O_4FS$, 492.1505. Found: 493.1504.

EXAMPLE 12

Cis-3-[[6-[(5-fluoro-2-benzothiazolyl)methoxy]-3,4-dihydro-4-hydroxy-2H-1-benzopyran-3-yl]methyl]-N-(2-thiazolyl)benzamide Synthesis was carried out as in example 1, but using 1.43 grams 2-aminothiazole instead of methane sulfonamide, and using 1.17 grams cis-4-nitrophenyl-3-[[6-[(5-fluoro-2-benzothiazolyl)methoxy]-3,4-dihydro-4-hydroxy-2H-1-benzopyran-3-yl]methyl]benzoate.

There was obtained 145 milligrams of product, m.p. 120° C.

Mass spectrum: Calculated for $C_{28}H_{23}N_3O_4FS_2$, 547.1009. Found, 547.1006.

EXAMPLE 13

Cis3-[[6-[(5-fluoro-2-benzothiazolyl)methoxy]-3,4-dihydro-4-hydroxy-2H-1-benzopyran-3-yl]methyl]-N-(3-thiopyridoyl)benzamide Synthesis was carried out as in example 1, but using 1.1 grams thionicotinamide instead of methane sulfonamide, and using 150 milligrams sodium hydride and 586 milligrams cis-4-nitrophenyl-3-[[6-[(5-fluoro-2-benzothiazolyl)methoxy]-3,4-dihydro-4-hydroxy-2H-1-benzopyran-3-yl]methyl]benzoate. There was obtained 170 milligrams of product as a foam.

EXAMPLE 14

Cis-3-[[6[(5-fluoro-2-benzothiazolyl)methoxy]-3,4-dihydro-4-hydroxy-2H-1-benzopyran-3-yl]methyl]-N-(4-methoxy-2-benzothiazolyl)benzamide Synthesis was carried out as in example 1, but using 2.56 grams 2-amino-4-methoxy benzothiazole, and using 1.17 grams cis-4-nitrophenyl-3-[[6-[(5-fluoro-2-benzothiazolyl)methoxy]-3,4-dihydro-4-hydroxy-2H-1-benzopyran-3-yl]methyl]benzoate. There was obtained 47 milligrams of product as a foam.

Mass spectrum: Calculated for $C_{25}H_{22}N_2O_5SF$, 62.1213. Found, 462.1209.

We claim:

1. A compound of the formula

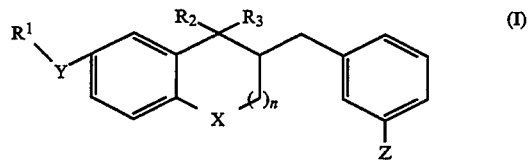

wherein $R^1$ is quinolyl, substituted quinolyl, benzothiazolyl, substituted benzothiazolyl, benzopyrimidinyl, substituted benzopyrimidinyl, wherein said substituted quinolyl, substituted benzothiazolyl, and substituted benzopyrimidinyl are substituted with one or more substituents that are independently selected from the group consisting of fluoro, bromo, chloro, phenyl, hydroxy, trifluoromethyl and ($C_1$-$C_4$)alkyl;

$R^2$ and $R^3$ are each H or OH;

Y is $CH_2O$, $C_2H_2$ or $C_2H_4$;

X is $CH_2O$, S, NH or $NR^7$;

$R^7$ is ($C_1$-$C_4$)alkyl;

n is an integer from 0-3; and

Z is CONHW, wherein

W is $SO_2Q$, COQ or Q, wherein

Q is hydrogen, phenyl, substituted phenyl, ($C_1$-$C_8$) alkyl, cycloalkyl, tetrazolyl, or thiazolyl, wherein the foregoing substituted phenyl groups are substituted with one or more substituents independently selected from the group consisting of chloro, fluoro and ($C_1$-$C_4$)alkoxy;

and the pharmaceutically acceptable acid addition and cationic salts thereof.

2. A compound according to claim 1, wherein $R^1$ is 5-fluoro 2-benzothiozolyl.

3. A compound according to claim 2, wherein X is O.

4. A compound according to claim 3, wherein R² is hydrogen, R³ is hydroxy and n is 1.

5. A compound according to claim 3, wherein Z is N-phenylsulfonyl carboxamide.

6. A compound according to claim I, said compound being selected from the group consisting of cis-3-[[6-[(5-fluoro-2-benzothiazolyl)methoxy]-3,4-dihydro-4-hydroxy-2H-1-benzopyran-3-yl]methyl]-N(methanesulfonyl)benzamide, cis-3-[[6-[5-fluoro-2benzothiazolyl)-methoxy]-3,4-dihydro-4-hydroxy-2H-1 -benzopyran-3-yl]methyl]-N-(acetyl)benzamide, cis-3- [[6-[(5-fluoro-2-benzothiazolyl)methoxy]-3,4-dihydro-4-hydroxy-2H-1-benzopyran-3-yl]methyl]-N-(2-methylbenzoylbenzamide, cis-3-[[6-[(5-fluoro-2-benzothiazoly)-methoxy]-3,4-dihydro-4-hydroxy-2H-1-benzopyran-3-yl ]methyl)-N-(phenylsulfonyl)benzamide, (+)-cis-3-[[6-[(5-fluoro-2-benzothiazolyl)methoxy]-3,4-dihydro-4-hydroxy-2H-1-benzopyran-3-yl]methoxy]-N-(methanesulfonyl)benzamide, (−)-cis-3-[[6-[(5-fluoro-2-benzothiazolyl)methoxy]-3,4-dihydro-4-hydroxy-2H-1-benzopyran-3-yl]methyl]-N-(methanesulfonyl)benzamide, cis-3-[[6-[(5-fluoro-2-benzothiazolyl)methoxy]-3,4-dihydro-4-hydroxy-2H-1-benzopyran-3-yl]methyl]-N-(tetrazolyl)benzamide, (+)-cis-3-[[6-[(5-fluoro-2-benzothiazolyl)-methoxy]-3,4 -dihydro-4-hydroxy-2H-1-benzopyran-3-yl]methyl]-N-(phenylsulfonyl)benzamide, (−)-cis-3-[[6-[(5-fluoro-2-benzothiazolyl)methoxy ]-3,4-dihydro-4-hydroxy-2H-1-benzopyran-3-yl]methyl]-N-(phenylsulfonyl)benzamide, cis-3-[[6-[(5-fluoro-2-benzothiazolyl)methoxy]-3,4-dihydro-4-hydroxy-2H-1-benzopyran-3-yl]methyl]benzamide, cis-3-[[6-[(5-fluoro-2-benzothiazolyl)methoxy]-3,4-dihydro-4-hydroxy-2H-1-benzopyran-3-yl]methyl]-N,N-dimethylbenzamide, cis-3-[[6-[(5-fluoro-2-benzothiazolyl)methoxy]-3,4-dihydro-4-hydroxy-2H-1-benzopyran-3-yl]methyl]-N-(2-thiazolyl)benzamide, cis-3-[[6-[(5-fluoro-2-benzothiazolyl)methoxy]-3,4dihydro-4-hydroxy-2H-1-benzopyran-3-yl]methyl]-N-(3-thiopyridoyl)benzamide, and cis-3-[[6[(5-fluoro-2-benzothiazolyl)methoxyl]-3,4-dihydro-4-hydroxy-2H-1-benzopyran-3-yl]methyl]-N-(4-methoxy-2-benzothiazolyl)benzamide.

7. A racemic or optically active compound according to claim 1 having the relative and absolute stereochemical formula

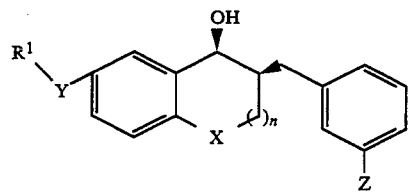

8. A racemic or optically active compound according to claim 1 having the relative and absolute stereochemical formula

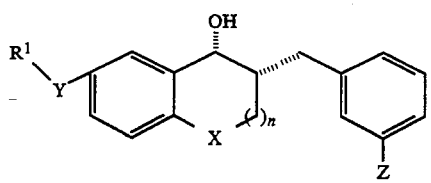

9. A pharmaceutical composition for the treatment or prevention of asthma, arthritis, psoriasis, gastrointestinal ulcers, myocardial infarction, stroke or irritable bowel disease, comprising an amount of a compound according to claim 1 effective in treating or preventing any one of said diseases.

10. A method for the treatment or prevention of asthma, arthritis, psoriasis, gastrointestinal ulcers, or myocardial infarction, stroke or irritable bowel disease comprising administering to a mammal in need of said treatment or prevention a compound according to claim 1 in an amount effective to treat or prevent any one of said diseases.

11. A method of inhibiting 5-lipoxygenase enzyme in a mammal, comprising administering to a mammal an amount of a compound according to claim 1 effective in inhibiting 5-lipoxygenase enzyme.

12. A method of blocking receptors of a leukotriene selected from the group consisting of leukotriene B4, leukotriene C4, leukotriene D4 and leukotriene E4, in a mammal comprising administering to a mammal an amount of a compound according to claim 1 effective in blocking receptors of any one of said leukotrienes.

* * * * *